(12) United States Patent
Tokuyasu et al.

(10) Patent No.: US 6,204,404 B1
(45) Date of Patent: Mar. 20, 2001

(54) PROCESS FOR PREPARING ESTER COMPOUNDS

(75) Inventors: Noriaki Tokuyasu; Shin Nakamura, both of Aichi (JP)

(73) Assignee: Daihachi Chemical Industry Co., Ltd., Osaka (JP)

(*) Notice: Subject to any disclaimer, the term of this patent is extended or adjusted under 35 U.S.C. 154(b) by 0 days.

(21) Appl. No.: 09/445,203

(22) PCT Filed: Jun. 5, 1998

(86) PCT No.: PCT/JP98/02519

§ 371 Date: Dec. 3, 1999

§ 102(e) Date: Dec. 3, 1999

(87) PCT Pub. No.: WO98/55486

PCT Pub. Date: Dec. 10, 1998

(30) Foreign Application Priority Data

Jun. 6, 1997 (JP) .................................................. 9-149676
Aug. 29, 1997 (JP) .................................................. 9-234254
Feb. 10, 1998 (JP) .................................................. 10-028587

(51) Int. Cl.[7] ................................ C07F 9/12; C07F 9/11; C07F 9/09
(52) U.S. Cl. ................................ 558/92; 558/94; 558/102
(58) Field of Search ................................ 558/92, 102, 94

(56) References Cited

U.S. PATENT DOCUMENTS 3,931,366 * 1/1976 Giolito et al. ........................ 558/146

FOREIGN PATENT DOCUMENTS

| 51-88994 | 4/1976 | (JP) . |
| 55-20772 | 2/1980 | (JP) . |
| 63-227632 | 9/1988 | (JP) . |
| 03193793 | 8/1991 | (JP) . |
| 3-182556 | 8/1991 | (JP) . |
| 5-1079 | 4/1993 | (JP) . |
| 8-67685 | 3/1996 | (JP) . |
| 8-283277 | * 10/1996 | (JP) . |

OTHER PUBLICATIONS

STN International CAPLUS Database, Chemical Anstracts Service, (Columbus, Ohio), Accession No. 1997:9428; abstract of JP 08–283277.*

* cited by examiner

Primary Examiner—Michael G. Ambrose
(74) Attorney, Agent, or Firm—Cohen, Pontani, Lieberman & Pavane

(57) ABSTRACT

A process for preparing an ester compound comprising reacting a halogen-substituted aliphatic hydroxy compound or aromatic hydroxy compound with a phosphorus oxyhalide or phosphorus pentahalide in the presence of 0.005 to 10 mol % of a phosphorus trihalide with respect to the hydroxy compound to obtain a phosphoric ester compound.

Phosphoric ester compounds of high purity containing less coloring components can be prepared without using an antioxidant.

17 Claims, No Drawings

PROCESS FOR PREPARING ESTER COMPOUNDS

FIELD OF THE INVENTION

The present invention relates to a process for preparing ester compounds. More particularly, it relates to a process for preparing phosphoric ester compounds of high purity containing less coloring components without using an antioxidant.

RELATED ART

Phosphoric ester compounds among ester compounds have been used not only as additives to various resins such as a plasticizer, a flame-retardant and a resin modifier but also as a lubricant and a stabilizer. On the other hand, according to recent technologic innovations in automobile industry, electronics and so forth, higher performances have been kept demanded with resins. From such background, phosphoric ester compounds having highly improved basic performances are required as the additives to resins, and a development of a new method for preparing such phosphoric ester compounds is requested by its industry.

The ester compounds are generally produced by reacting a hydroxy compound with an acid or its reactive derivative in the presence or absence of a condensating agent such as sulfuric acid and p-toluenesulfonic acid. However, when the reactivity of these starting materials in the aforesaid reaction is not sufficient, the reaction needs to be conducted at a high temperature. In such case, particularly in the case where the ester compound is to be produced in industrial scale and an impurity is contained in the hydroxy compound of the starting material, it causes the coloration of the desired ester compound.

To solve such problem, for example, an antioxidant is added into the reaction system in order to prevent an oxidation of an impurity contained in the hydroxy compound as the starting material. Further, various antioxidants are put into market. This suggests that addition of the antioxidant is an effective means for preventing the coloration of the ester compound.

However, antioxidants on the market are expensive and a cost for product rises when antioxidants are used in preparing the ester compound, which causes economical disadvantage. Moreover, it is a difficult and complicated work to select an optimum condition for using antioxidants.

Japanese Unexamined Patent Publication No. SHO 51 (1976)-88944 discloses a treatment method for preventing coloration of alkyliphenyl phosphates. This publication discloses addition of an effective amount of phosphorus trichloride to an alkylated mixture in the case of producing an alkylphenyl phosphate by adding an olefin to phenol, then adding phosphorus oxychloride thereto and reacting the mixture in the presence of Friedel-Crafts catalyst under warming.

Further, this publication also describes that phenols having alkyl groups at both ortho positions with respect to hydroxyl group, that is, hindered phenols become quinones through oxidation in the presence of air, and that these phenols cause coloring of the ester compounds when these phenols are used for synthesizing the ester compounds.

Another problem in addition to the above-described coloration is as follows. That is, purification by a crystallization method is regarded as essential for preparing tris (tribromoneopentyl)phosphate as phosphoric ester compound of high quality. However, the crystallization method is complicate for operation, requires an apparatus of a large scale, and results in much loss of product. Therefore, a use of the crystallization method is disadvantageous in industrial production of tris(tribromoneopentyl)phosphate, resulting in an increase of the cost for product.

DISCLOSURE OF THE INVENTION

It is a subject of the present invention to provide a process for preparing phosphoric ester compounds of high purity containing less coloring components without using an antioxidant.

That is, according to the present invention, provided is a process for preparing an ester compound comprising reacting a halogen-substituted aliphatic hydroxy compound or aromatic hydroxy compound with a phosphorus oxyhalide or phosphorus pentahalide in the presence of 0.005 to 10 mol % of a phosphorus trihalide with respect to the said hydroxy compound to obtain a phosphoric ester compound.

DESCRIPTION OF THE PREFERRED EMBODIMENTS

The halogen-substituted aliphatic hydroxy compounds or the aromatic hydroxy compounds to be used in the present invention are not particularly limited. However, even if the hydroxy compounds contain impurities resulted from a preparing process thereof (for example, aldehydes or the like), such hydroxy compounds may suitably be used for the process of the present invention.

Further, in the case of synthesizing general-purpose phosphoric ester compounds used as additives to resins, halogen-substituted aliphatic hydroxy compounds of 4 to 20 carbon atoms or aromatic hydroxy compounds of 6 to 20 carbon atoms may be used.

The halogen-substituted aliphatic hydroxy compounds are aliphatic hydroxy compounds substituted by a halogen atom such as chlorine atom, bromine atom or the like. Specifically, chloromethyl alcohol, 2-chloroethyl alcohol, 1-chloro-2-propanol, 3-bromo-2,2-dimethyl-1-propanol [bromoneopentyl alcohol], 2-bromomethyl-3-bromo-2-methyl-1-propanol [dibromoneopentyl alcohol] and 2,2-di(bromomethyl)-3-bromo-1-propanol [tribromoneopentyl alcohol] are mentioned.

In the present invention, "the aromatic hydroxy compounds" mean mono- or polyvalent phenols which may be substituted by other substituent than alkyl group. Specific examples are given as follows;

aromatic hydroxy compounds such as; monovalent phenols such as phenol, (2-, 3-, or 4-)phenylphenol [oxybiphenyl] and (1- or 2-)naphthol; and substituted phenols such as chlorophenol, dichlorophenol, trichlorophenol, bromophenol, dibromophenol, tribromophenol and nitrophenol; and aromatic dihydroxy compounds such as; polyvalent phenols such as catechol, resorcinol (resorcin), hydroquinone, pyrogallol and fluloroglucinol; and bisphenols such as 2,2-bis(4'-oxyphenyl)propane [bisphenol A], bis(4-hydroxyphenyl) sulfone [bisphenol S] and biphenyldiol.

In the case where the above-mentioned hydroxy compounds are used solely, phosphoric triester compounds can be obtained. Also when two or more kinds of the hydroxy compounds are reacted stepwise, mixed phosphoric ester compounds and condensed phosphoric ester compounds can be obtained.

Among the above-mentioned hydroxy compounds, the halogen-substituted aliphatic hydroxy compounds such as tribromoneopentyl alcohol and the aromatic hydroxy compounds such as phenol, resorcinol and hydroquinone are particularly preferable.

In the process of the present invention, the phosphorus oxyhalide or phosphorus pentahalide is used. Examples of the phosphorus oxyhalide are phosphorus oxychloride and phosphorus oxybromide. Examples of the phosphorus pentahalide are phosphorus pentachloride and phosphorus pentabromide. Among them, in the case where phosphoric ester compounds are produced industrially, phosphorus oxychloride can generally and preferably be used.

The present invention is characterized by adding the phosphorus trihalide when phosphoric ester compounds are produced using the above-described starting materials.

As the phosphorus trihalide, phosphorus trichloride and phosphorus tribromide are preferable, and can be used just as they are on the market or after purification as the needs arise. Further, in the case of industrial production of the phosphoric ester compounds, phosphorus trichloride can generally and preferably be used. Additionally, phosphorous acid can be used instead of the phosphorus trihalide.

The addition amount of the phosphorus trihalide varies in accordance with the types of the hydroxy compounds as the starting materials and the combination with the phosphorus oxyhalide or the phosphorus pentahalide, but generally, the amount of the phosphorus trihalide with respect to the hydroxy compound is 0.005 to 10 mol %, preferably 0.01 to 5 mol %, and more preferably 0.02 to 2 mol %.

When the above-mentioned addition amount is less than 0.005 mol %, it is not preferable because the prevention effect for coloration is not sufficiently obtained in the reaction. On the other hand, when the addition amount is more than 10 mol %, it is uneconomical because greater effect cannot be expected.

Additionally, by adjusting the addition amount within the above-mentioned range, thermostability, oxidation stability and resistance to the coloration of the phosphoric ester compounds to be obtained can be controlled.

As usage patterns of the phosphorus trihalide, there may be mentioned;

① a method wherein the phosphorus trihalide is added to a mixture of the halogen-substituted aliphatic hydroxy compound or aromatic hydroxy compound with the phosphorus oxyhalide or phosphorus pentahalide; and ② a method wherein the phosphorus oxyhalide or phosphorus pentahalide is added to a mixture of the said hydroxy compound with the phosphorus trihalide.

In the reaction of the present invention, a catalyst and a solvent may be used as required.

Examples of the catalysts are metallic chloride such as aluminum chloride, magnesium chloride and zinc chloride, among which aluminum chloride and magnesium chloride are preferable. These catalysts may be added in the reaction system with a required amount.

Also, the solvent is not particularly limited as long as it is inert under the reaction condition of the present invention. Its examples are aliphatic hydrocarbons such as n-hexane, n-heptane and cyclohexane; aromatic hydrocarbons such as benzene, toluene, (o-, m-, p-)xylene, ethylbenzene and isopropylbenzene; halogenated aliphatic hydrocarbons such as dichloromethane, carbon tetrachloride and 1,2-dichloroethane; and halogenated aromatic hydrocarbons such as chlorobenzene, 1,2-dichlorobenzene, 2-fluorotoluene and bromobenzene, among which 1,2-dichlorobenzene and toluene are preferable.

The reaction condition according to the preparing process of the present invention is appropriately selected and utilized from known techniques. For example, the phosphorus oxyhalide or phosphorus pentahalide is used with one or a little excess chemical equivalent with respect to one chemical equivalent of the halogen-substituted aliphatic hydroxy compound or aromatic hydroxy compound.

The reaction temperature varies in accordance with the type and amount of the starting materials, but is generally at about 10 to 220° C., preferably at about 30 to 200° C.

The reaction time varies in accordance with the type and amount of the starting materials, the reaction temperature and the like. For preparing a product of good quality, the reaction time is in the range of about 0.5 to 20 hours.

In the case where the starting materials have a high activity and the reaction is exothermic, the reaction system may be cooled by conventional means. Hydrogen halide, water and the like which are produced as by-products in this reaction can be recovered by conventional means.

As the phosphoric ester compounds to be obtained in the process of the present invention may be mentioned the phosphoric triester compounds as obtained by reacting the halogen-substituted aliphatic hydroxy compound alone or the aromatic hydroxy compound alone or the mixed phosphoric ester compounds and condensed phosphoric ester compounds as obtained by reacting stepwise two or more types of the said hydroxy compounds.

The phosphoric triester compounds can be obtained under the above-mentioned reaction condition.

The mixed phosphoric ester compound can be obtained, for example, by subjecting the phosphorus oxyhalide and two or more types of the hydroxy compounds to dehydrohalogenation simultaneously or separately. In the case of separate dehydrohalogenation, unreacted phosphorus oxyhalide and hydrogen halide may be removed from the reaction mixture after the first reaction. In this case, the desired mixed phosphoric ester compound can be obtained by changing the type and amount of the hydroxy compounds optionally. The reaction condition is as described above.

Also, the condensed phosphoric ester compounds can be obtained, for example, by subjecting a phosphorus oxyhalide and an aromatic dihydroxy compound to dehydrohalogenation to yield an intermediate (a first reaction), and subjecting the intermediate and a hydroxy compound to dehydrohalogenation after removal of unreacted phosphorus oxyhalide and hydrogen halide from the reaction mixture (a second reaction). The reaction conditions are as described above, and the desired condensed phosphoric ester compounds can be obtained by changing the reaction conditions and the ratio of the starting materials optionally.

An example for obtaining the condensed phosphoric ester compounds is described below.

First, 1.1 mol of resorcinol are reacted with 3 mol of excessive phosphorus oxychloride in the presence of phosphorus trichloride and magnesium chloride, during which hydrogen chloride generated is recovered. Then after an excess of phosphorus oxychloride is removed, the obtained reaction mixture is reacted with 4 mol of phenol, while hydrogen chloride generated is removed, thereby obtaining the condensed phosphoric ester compound.

The phosphoric triester compounds, mixed phosphoric ester compounds and condensed phosphoric ester compounds to be obtained by the process of the present invention are represented by the general formula (I):

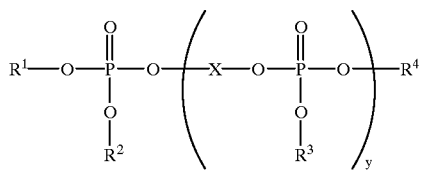

(I)

, wherein $R^1$ to $R^4$ are, the same or different, an alkyl group of 1 to 10 carbon atoms substituted by a halogen atom, or an aryl group of 6 to 12 carbon atoms which may be substituted by other substituent than alkyl group, X is a bivalent residue corresponding to hydroquinone, resorcinol, bisphenol A, bisphenol S or (2,2'-, 3,3'- or 4,4'-) biphenyldiol, and y is an integer from 0 to 10.

The "alkyl group of 1 to 10 carbon atoms substituted by a halogen atom" in the general formula (I) is an alkyl group of 1 to 10 carbon atoms substituted by a halogen atom such as chlorine atom and bromine atom, and preferably, butoxyethyl, bromoneopentyl, dibromoneopentyl and tribromoneopentyl.

As the "aryl group of 6 to 12 carbon atoms which may be substituted by other substituent than alkyl group" in the general formula (I), phenyl, biphenylyl, (1-, 2-)naphthyl, bromophenyl and tribromophenyl may be mentioned.

As the substituents $R^1$ to $R^4$, tribromoneopentyl and phenyl are preferable, and as for the substituent X, the bivalent residues corresponding to hydroquinone and resorcinol are preferable.

Y in the general formula (I) is an integer from 0 to 10, and in particular, 0 and 1 are preferable.

Specific examples of the compounds represented by the general formula (I) are: phosphoric triesters such as triphenyl phosphate, tris(bromophenyl)phosphate, tris(tribromophenyl)phosphate, tris(bromoneopentyl)phosphate, tris(dibromoneopentyl)phosphate and tris(tribromoneopentyl)phosphate; and condensed phosphoric ester compounds such as hydroquinone bis(diphenyl phosphate), resorcinol bis(diphenyl phosphate), bisphenol A bis(diphenyl phosphate) and bisphenol A bis(dicresyl phosphate).

The process of the present invention can suitably be used for preparing tris(tribromoneopentyl)phosphate and resorcinol bis(diphenyl phosphate), which have heretofore accompanied with remarkable coloration due to synthesis method thereof.

The obtained phosphoric ester compounds are taken out from reactor, and may be made up by removing the catalyst and solvent and purifying with known methods such as alkali neutralization, filtration, washing, distillation and the like. In the case where the ester compounds are haloalkyl phosphoric ester compounds or the condensed phosphoric ester compounds to be described later, the ester compounds can be purified by a crystallization method, for example, as described in Example 1 of Japanese Unexamined Patent Application No. Hei 3(1991)-193793. According to this method, the reaction mixture is contacted with water under stirring at 60 to 100° C. and cooled to room temperature to precipitate crystals. Then the precipitated crystals are isolated by filtration, washed with methanol, and dried under a reduced pressure.

Also, waste water which generated during the above-described purification of the phosphoric triester compound and indicated a certain COD value is usually changed to be nonpolluting by subjecting a biodegradation treatment.

However, waste water generated in the process for preparing the haloalkyl phosphoric ester compound and condensed phosphoric ester compound contains materials slow or hard to degrade which are not suitable for the biodegradation treatment. In such a case, the waste water can be nonpolluting by subjecting to a spray dryer after being condensed by a distillation apparatus as required.

Alternatively, tris(tribromoneopentyl)phosphate can be washed with water or an acid or alkaline solution without purification by the crystallization method as described above, thereby yielding the phosphate of high quality in good yield. Such washing method can be readily operated without using an apparatus of a large scale for the crystallization method, and hence is advantageous in industrial production, achieving low cost for product.

Hereinafter, washing of tris(tribromoneopentyl) phosphate, is examplified.

①  First, to the reaction mixture containing tris(tribromoneopentyl) phosphate added is the same solvent as used in the reaction in an amount of 2 to 5 times by weight ratio larger than the tris(tribromoneopentyl) phosphate.

②  The resulting mixture is added with an acid aqueous solution such as 0.7% HCl aqueous solution in an amount of 0.1 to 2 times by weight ratio larger than tris(tribromoneopentyl)phosphate at a temperature of 60 to 95° C., stirred for 10 to 60 minutes and allowed to stand to separate an aqueous phase to be drained.

③  Then, the remaining is added with an alkaline aqueous solution such as 0.7% $Na_2CO_3$ aqueous solution in an amount of 0.1 to 2 times by weight ratio larger than the tris(tribromoneopentyl)phosphate at a temperature of 60 to 95° C., stirred for 10 to 60 minutes and allowed to stand to separate the aqueous phase to be drained, and ④  Then, the remaining is added with water at 90° C. in an amount of 0.1 to 2 times by weight ratio larger than the tris(tribromoneopentyl)phosphate, stirred for 10 to 60 minutes and allowed to stand to separate the aqueous phase to be drained.

Tris(tribromoneopentyl)phosphate can be obtained by subjecting the resultant oily phase to a treatment for removing the solvent, for example, using a rotary evaporator or the like.

An action mechanism of the phosphorus trihalide in the present invention is not clear, but it is considered that in preparing phosphoric ester compounds, the phosphorus trihalide is reacted with the hydroxy compound to produce a phosphite, which functions as an antioxidant against impurity contained in the hydroxy compound of the reaction system to prevent generation of coloring components except the desired ester compound.

Further, for the production of the phosphoric ester compounds, the produced phosphite is gradually oxidized by dissolved oxygen in the reaction mixture or oxygen in air to become a phosphoric ester compound. The phosphoric ester compound produced through the oxidation of the phosphite is an analogue having the same residue of the hydroxy compound as the phosphoric ester compound which is a main product, and exists in the corresponding phosphoric ester compound. However, in comparison with conventionally added thermostabilizer and antioxidant, the physical property of the phosphoric ester compound is hardly affected harmfully.

Particularly, in the case where the phosphoric ester compound is prepared from the hydroxy compound and the phosphorus oxyhalide, the added phosphorus trihalide finally becomes a phosphoric ester compound itself which is a main product, and thus the desired phosphoric ester compound can be obtained in high purity. Accordingly, the reaction of this combination is the most preferable embodiment of the present invention.

EXAMPLES

The present invention will be described in detail by the following examples. These examples will not limit the scope of the present invention.

The obtained ester compounds are evaluated by the following methods.

① A heat test

The heat test was performed under an air atmosphere and the conditions shown in Table 1 [temperature (° C.)×time].

② Hues before and after the heat test

As to the ester compounds described in Examples 2 and 3 and Comparative Example 1, 200 g of the ester compounds were dissolved in one liter of THF (tetrahydrofuran), and then the hue thereof was measured. As to the ester compound of Example 1, the hue of the compound itself was measured.

③ A purity and an average molecular weight

The purity and the average molecular weight were measured by gel permeation chromatography (GPC).

Example 1

121 g (1.1 mol) of resorcinol and 460 g (3 mol) of phosphorus oxychloride were placed in a four-necked flask equipped with a stirrer, a thermometer and a Dimroth condenser connecting to an apparatus for recovering hydrogen chloride, and then heated up to 50° C. with stirring. Further, 1 g (0.8 mol % with respect to resorcinol) of phosphorus trichloride was added thereto and stirred at 50° C. for 0.5 hours. Then, 3 g of magnesium chloride were added as a catalyst, followed by heating up to 105° C. with stirring for three hours. Hydrogen chloride generated in this process was recovered into the apparatus for recovering hydrogen chloride (recovered amount of 75 g). Thereafter, an excess of phosphorus oxychloride was removed by treating at a temperature of 105° C. under a pressure of 20 Torr for four hours, and then the pressure was returned to the normal pressure.

380 g (4 mol) of phenol were added to the obtained reaction mixture, followed by heating up to 150° C. again. Hydrogen chloride generated in this process was recovered into the apparatus for recovering hydrogen chloride (recovered amount of 126 g). Then 593 g of the reaction mixture were obtained by treating at 150° C. under a pressure of 20 Torr for four hours. Any phosphite compounds were not detected in the reaction mixture at this time. The concentration of the phosphite compound was measured by a method wherein iodine consumed by the phosphite was titrated with sodium thiosulfate.

The reaction mixture was subjected to a purification and neutralization treatment. 570 g of condensed phosphoric ester compound as the final product were obtained, which is represented by the following formula (yield 90.3%)

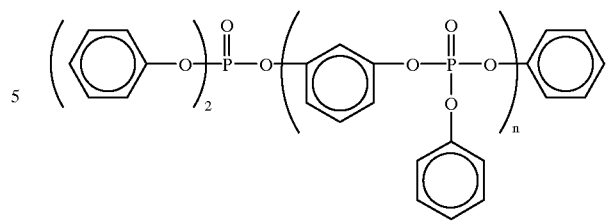

, wherein n is an integer from 1 to 6.

Physical properties of the obtained condensed phosphoric ester compound are shown in Table 1 and the below.

| Appearance | light yellow transparent liquid |
| --- | --- |
| Hue | Hz = 20 |
| Average molecular weight | 510 |
| Acid value | 0.03 |
| Purity | 70.0% (n = 1) |

Example 2

2925 g (9 mol) of tribromoneopentyl alcohol and 1500 g of 1,2-dichlorobenzene as a solvent were placed in a four-necked flask equipped with a stirrer, a thermometer and a Dimroth condenser connecting to an apparatus for recovering hydrogen chloride. 1 g (0.03 mol % with respect to tribromoneopentyl alcohol) of phosphorus trichloride was added thereto and stirred at 50° C. for 0.5 hours. Then, 2 g of aluminum chloride as a catalyst and 460 g (3 mol) of phosphorus oxychloride were added, followed by heating up to 150° C. with stirring for three hours. Hydrogen chloride generated in this process was recovered into the apparatus for recovering hydrogen chloride (recovered amount of 3110 g). Thereafter, 4548 g of the reaction mixture whose appearance was yellow was obtained by treating at a temperature of 180° C. under a pressure of 100 Torr for three hours.

This reaction mixture was purified by the crystallization method described in Example 1 of Japanese Unexamined Patent Application No. Hei 3(1991)-193793. That is, the obtained reaction mixture was cooled to 85° C. Then, 190 g of water were added thereto, stirred to contact the water with the reaction mixture at 85° C. for about 20 minutes and cooled to room temperature to precipitate crystals. The precipitated crystals were isolated by filtration, washed with 1150 g of methanol and dried at 100° C. under a reduced pressure. The obtained crystals were subjected to a flaking thereby to obtain 3054 g of tris (tribromoneopentyl) phosphate as the final product (yield 99.9%).

The physical properties of the obtained tris (tribromoneopentyl) phosphate are shown in Table 1 and the below.

| Appearance | white powder |
| --- | --- |
| Hue of solution | Hz = 40 |
| Acid value | 0.53 |
| Purity | 97.8% |

Comparative Example 1

The phosphoric ester compound was synthesized in the same manner as Example 2 except that phosphorus trichloride was not used. Recovered amount of hydrogen chloride during synthesis was 312 g. The obtained reaction mixture weighed 4543 g and the appearance thereof was blackish brown.

The reaction mixture was subjected to a purification and flaking, then 3052 g of tris(tribromoneopentyl)phosphate as the final product was obtained (yield 99.8%).

The physical properties of the obtained tris (tribromoneopentyl) phosphate are shown in Table 1 and the below.

| | Appearance | | ashen powder | | |
|---|---|---|---|---|---|
| | Hue of solution | | Hz = 800 | | |
| | Acid value | | 0.55 | | |
| | Purity | | 97.2% | | |
| | | before Heat test | | after Heat test | |
| No. | Heat test conditions temperature (° C.) × hour(s) | hue (Hz) | acid value (KOH mg/g) | hue (Hz) | acid value (KOH mg/g) |
| Example 1 | 250 × 3 | 20 | 0.03 | <1 (G) | 0.7 |
| Example 2 | 250 × 3 | 40 | 0.53 | — | — |
| Comparative Example 1 | 250 × 3 | >800 | 0.55 | — | — |

Example 3

752 g (2.31 mol) of tribromoneopentyl alcohol and 1075 g of 1,2-dichlorobenzene as a solvent were placed in a four-necked flask equipped with a stirrer, a thermometer and a Dimroth condenser connecting to an apparatus for recovering hydrogen chloride, and heated up to 100° C. with stirring. Then 1.2 g of aluminum chloride as a catalyst and 2 g (0.63 mol % with respect to tribromoneopentyl alcohol) of phosphorus trichloride were added and 120 g (0.78mol) of phosphorus oxychloride was further added, followed by heating up to 160° C. with stirring for two hours. Hydrogen chloride generated in this process was recovered into the apparatus for recovering hydrogen chloride (recovered amount of 81.0 g). Thereafter, the reaction mixture was treated at a temperature of 140° C. under a pressure of 220 Torr for four hours. Thus, 1860 g of the reaction mixture whose appearance was yellow and transparent were obtained.

2500 g of 1,2-dichlorobenzene were added to this reaction mixture, and then the mixture was washed with the below-described steps of:

(1) adding 300 g of 0.7% HCl aqueous solution to the mixture at 90° C., stirring for 30 minutes, allowing to stand to separate the aqueous phase (pH 1), which was drained, (2) then, adding 300 g of 0.7% Na₂CO₃ aqueous solution to the oily phase at 90° C., stirring for 30 minutes and allowing to stand to separate the aqueous phase (pH 9), which was drained, (3) further, adding 300 g of water at 90° C. to the oily phase, stirring for 30 minutes and allowing to stand to separate the aqueous phase (pH 7), which was drained.

The resulting liquid was subjected to a rotating evaporator for removing the solvent, thereby to obtain 777 g of tris (tribromoneopentyl)phosphate as the final product (yield 98.0%).

The physical properties of the obtained tris (tribromoneopentyl) phosphate are shown below.

| Appearance | white powder |
|---|---|
| Hue of solution | Hz = 10 |
| Acid value | 0.02 |
| Purity | 99.2% |

As is obvious from the results of Examples 2 and 3, according to the process of the present invention, tris (tribromoneopentyl)phosphate of high quality and in high yield can be obtained by merely washing with an acid aqueous solution, an alkaline aqueous solution and water, without using a crystallization process.

A process for preparing an ester compound of the present invention is characterized by reacting a halogen-substituted aliphatic hydroxy compound or aromatic hydroxy compound with a phosphorus oxyhalide or phosphorus pentahalide in the presence of 0.005 to 10 mol % of a phosphorus trihalide with respect to the hydroxy compound to obtain phosphoric ester compounds.

Therefore, the phosphoric ester compound of high purity containing less coloring components can be prepared without using an antioxidant.

Further, since phosphorus trichloride and phosphorus tribromide are inexpensive and readily available, the present invention has an advantage in producing phosphoric ester compounds industrially compared with the conventional methods using an expensive antioxidant. Additionally, since a complicated process to set conditions for using the antioxidant in the most suitable way is not necessary, development of a new product is expedited, and the present invention has a greater utility value in industrial field.

More further, in the case of preparing tris (tribromoneopentyl) phosphate, the product of high quality and in high yield can be obtained because a purification by crystallization method in which product will be lost largely is not necessary.

What is claimed is:

1. A process for preparing an ester compound comprising adding phosphorus trihalide to a mixture of at least one of a halogen-substituted aliphatic hydroxy compound, an aromatic hydroxy compound which may be substituted by substituents other than an alkyl group, and an aromatic dihydroxy compound selected from the group consisting of hydroquinone, resorcinol, bisphenol A, bisphenol S and (2,2'-, 3,3'- and 4,4'-biphenyldiol or a mixture thereof, with a phosphorus oxyhalide or phosphorus pentahalide, wherein the phosphorus trihalide is added in the amount of 0.005 to 10 mol % of the hydroxy compound to obtain a phosphoric ester compound represented by the general formula (I):

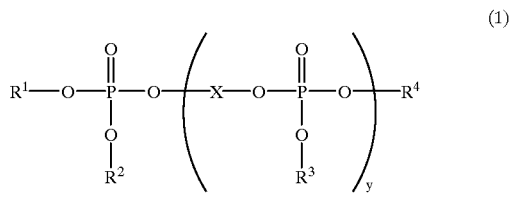

wherein $R^1$, $R^2$, $R^3$ and $R^4$ are, the same or different, an alkyl group of 1 to 10 carbon atoms substituted by a halogen atom, or an aryl group of 6 to 12 carbon atoms which may be substituted by substituents other than an alkyl group, X is a bivalent residue corresponding to hydroquinone, resorcinol, bisphenol A, bisphenol S or (2,2'-, 3,3'- or 4,4'-) biphenyldiol, and y is an integer from 0 to 10.

2. A process according to claim 1, wherein the phosphorus trihalide is phosphorus trichloride or phosphorus tribromide.

3. A process according to claim 1, wherein the phosphorus oxyhalide is phosphorus oxychloride.

4. A process according to claim 1, wherein a phosphoric triester compound is obtained by reacting a halogen-substituted aliphatic hydroxy compound or an aromatic hydroxy compound alone.

5. A process according to claim 1, wherein the halogen-substituted aliphatic hydroxy compound is tribromoneopentyl alcohol.

6. A process according to claim 5, wherein the ester compound is tris(tribromoneopentyl)phosphate.

7. A process according to claim 1, wherein mixed phosphoric ester compounds are obtained by reacting the phosphorus oxyhalide with two or more halogen-substituted aliphatic hydroxy compounds or aromatic hydroxy compounds which may be substituted by substituents other than an alkyl group.

8. A process according to claim 1, wherein the phosphorus oxyhalide and the aromatic dihydroxy compound are first reacted to obtain an intermediate compound, then the intermediate compound and halogen-substituted aliphatic hydroxy compound or aromatic hydroxy compound which may be substituted by substituents other than an alkyl group are reacted after removal of unreacted phosphorus oxyhalide and hydrogen halide from the reaction mixture to obtain a condensed phosphoric ester compound.

9. A process according to claim 8, wherein the aromatic dihydroxy compound is resorcinol or hydroquinone, and the aromatic hydroxy compound is phenol.

10. A process according to claim 9, wherein the ester compound is resorcinol bis(diphenyl phosphate).

11. A process according to claim 1, wherein the reaction is conducted in a solvent.

12. A process according to claim 1, wherein the solvent is 1,2-dichlorobenzene.

13. A process according to claim 1, wherein the reaction is conducted in the presence of a catalyst.

14. A process according to claim 13, wherein the catalyst is aluminum chloride or magnesium chloride.

15. A process according to claim 1, wherein the ester compound is further subjected to a crystallization treatment.

16. A process according to claim 6, comprising further washing the tris(tribromoneopentyl)phosphate with an acid aqueous solution, an alkaline aqueous solution and water.

17. A process for preparing an ester compound comprising adding phosphorus oxyhalide or phosphorus pentahalide to a mixture of at least one of a halogen-substituted aliphatic hydroxy compound, an aromatic hydroxy compound which may be substituted by substituents other than an alkyl group, and an aromatic dihydroxy compound selected from the group consisting of hydroquinone, resorcinol, bisphenol A, bisphenol S and (2,2'-, 3,3'- and 4,4'-)biphenyldiol or a mixture thereof, with a phosphorus trihalide, wherein the phosphorus trihalide is in the amount of 0.005 to 10 mol % of the hydroxy compound to obtain a phosphoric ester compound represented by the general formula (I):

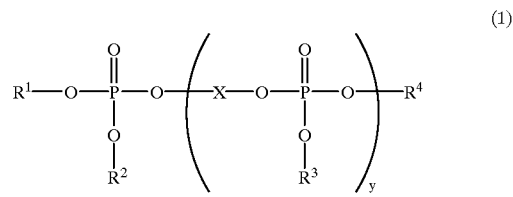

wherein $R^1$, $R^2$, $R^3$ and $R^4$ are, the same or different, an alkyl group of 1 to 10 carbon atoms substituted by a halogen atom, or an aryl group of 6 to 12 carbon atoms which may be substituted by substituents other than an alkyl group, X is a bivalent residue corresponding to hydroquinone, resorcinol, bisphenol A, bisphenol S or (2,2'-, 3,3'- or 4,4'-) biphenyldiol, and y is an integer from 0 to 10.

* * * * *